United States Patent [19]

Grimminger et al.

[11] Patent Number: 4,780,476
[45] Date of Patent: Oct. 25, 1988

[54] AZONIASPIRONORTROPANOL ESTERS AS ASTHMA THERAPEUTICS AND BRONCHOLYTICS

[75] Inventors: Wolf Grimminger, Gladbach; Karl P. Odenthal, Grevenbroich, both of Fed. Rep. of Germany

[73] Assignee: Madaus GmbH & Co., Cologne, Fed. Rep. of Germany

[21] Appl. No.: 945,773

[22] Filed: Dec. 23, 1986

[30] Foreign Application Priority Data

Dec. 27, 1985 [DE] Fed. Rep. of Germany ....... 3546165

[51] Int. Cl.[4] .............................................. A61K 31/40
[52] U.S. Cl. .................................... 514/409; 514/826
[58] Field of Search ................................ 514/409, 826

[56] References Cited

PUBLICATIONS

Lux et al, Chemical Abstracts, 90:48605m, 1979.
Keighley, Ann. Int. Med 65(5): 985-995 (Nov. 1966).
Speizer, et al, Brit. J. Med 1: 335-339 (Feb. 10, 1968).
Van Rossum et al., Arch. Int. Pharmacodyn. 143 (3-4): 299-330 (1963).

Primary Examiner—Leonard Schenkman
Attorney, Agent, or Firm—Felfe & Lynch

[57] ABSTRACT

The present invention is concerned with the use of azoniaspironortropanol esters of the general formula:

(I)

wherein R signifies one of the following radicals:
(a) an alkylene radical of the general formula:

$$-(CH_2)_n-CH(R_3)-(CH_2)_n-$$

in which $R_3$ is a hydrogen atom or an alkyl, benzyl, aryl or alkoxy radical and n is a whole number of from 1 to 4, (b) an alkenyl radical of the general formula:

$$-(CH_2)_n\phantom{xx}C=C\phantom{xx}(CH_2)_n-$$
$$\phantom{xxxxxx}R_4\phantom{xxxx}R_5$$

in which $R_4$ and $R_5$, which can be the same or different, are hydrogen atoms or alkyl or alkenyl radicals and n is a whole number of from 1 to 4, (c) an azaalkylene radical of the general formula:

$$-(CH_2)_n-N(R_6)-(CH_2)_n-$$

in which $R_6$ is a hydrogen atom or an alkyl, alkoxycarbonyl or acyl radical and n is a whole number of from 2 to 4, (d) an oxaalkylene radical of the general formula:

$$-(CH_2)_n-O-(CH_2)_n-$$

in which n is a whole number of from 2 to 4, (e) an epoxyalkylene radical of the formula:

$$-CH_2-CH\underset{O}{-\!\!-\!\!-}CH-CH_2-$$

(Abstract continued on next page.)

(f) an o-phenylene radical of the general formula:

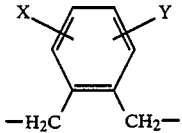

(g) a per-naphthylene radical of the general formula:

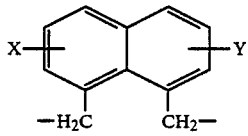

or
(h) a 2,3-quinoxalinene radical of the general formula:

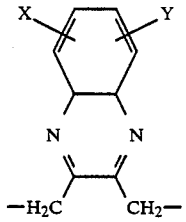

in which in formulae (f) to (h), the symbols X and Y, which can be the same or different, are hydrogen atoms or alkyl or alkoxy radicals;

and wherein $R_1$ and $R_2$, which can be the same or different, are hydrogen or halogen atoms or alkyl, alkoxy, alkoyl, cyclohexyl, phenyl, alkylphenyl, alkoxyphenyl, halophenyl, thienyl or furyl radicals, the alkyl moieties in the said radicals containing up to 6 carbon atoms and being straight-chained or branched, and $A^\ominus$ is the anion of a mono- to tribasic mineral acid, as asthma therapeutics or broncholytics.

9 Claims, 2 Drawing Sheets

AZONIASPIRONORTROPANOL ESTERS AS ASTHMA THERAPEUTICS AND BRONCHOLYTICS

The present invention is concerned with the use of azoniaspironortropanol esters as therapeutic agents for the treatment of asthma and as broncholytics.

In principle, there are three possible approaches to the treatment of diseases due to asthma and for bronchial diseases: cortisone or corticosteroids, sympathomimetics and parasympatholytics. As is known, corticosteroids produce serious side effects, including susceptibility to infections. Sympathomimetics also have considerable symptomatic side effects, for example tachycardia. Parasympatholytics, on the other hand, are characterized by a good measure of success, especially when administered locally, in that side effects are absent or minimal. However, the therapeutic results are not uniform and not certain because of differing response, depending on symptoms of the disease. In this regard, reference is made to J. F. Keighley, Iatrogenic asthma associated with adrenergic aerosols, Ann. intern. Med., 65, 985/1966 and F. E. Speizer et al., Observations on recent increase in mortality from asthma, B.M.J., 1, 335/1968.

It is known that some azoniaspironortropane derivatives possess spasmolytic properties (see Federal Republic of Germany Patent Specification No. 11 94 422 and Arzneimittelforschung, 17, 714–719/1967). However, these compounds have hitherto only been used in the urogenital region.

There is need for new asthma therapeutics and broncholytics with a parasympatholytic character of action but without a systemic accompanying action, i.e, without effect on circulatory regulation, and with dependable action.

It is an object of the present invention to improve the treatment of asthmatic diseases and of diseases of the bronchial region.

Thus, the present invention embraces a method of treating asthmatic diseases and diseases of the bronchial region via administration of azoniaspironortropanol esters of the formula:

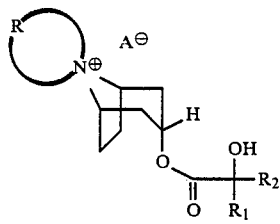

(I)

wherein R signifies one of the following radicals:

(a) an alkylene radical of the general formula:

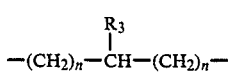

in which $R_3$ is a hydrogen atom or an alkyl, benzyl, aryl or alkoxy radical and n is a whole number of from 1 to 4, (b) an alkenylene radical of the general formula:

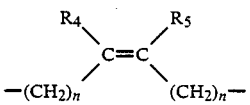

in which $R_4$ and $R_5$, which can be the same or different, are hydrogen atoms or alkyl or alkenyl radicals and n is a whole number of from 1 to 4, (c) an azaalkylene radical of the general formula:

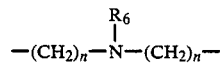

in which $R_6$ is a hydrogen atom or an alkyl, alkoxy-carbonyl or acyl radical and n is a whole number of from 2 to 4, (d) an oxaalkylene radical of the general formula:

$$-(CH_2)_n-O-(CH_2)_n-$$

in which n is a whole number of from 2 to 4, (e) an epoxyalkylene radical of the formula:

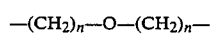

(f) an o-phenylene radical of the general formula:

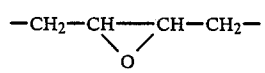

(g) a peri-naphthylene radical of the general formula:

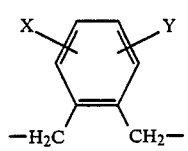

or (h) a 2,3-quinoxalinene radical of the general formula:

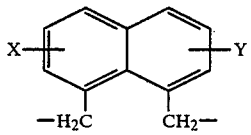

in which in formulae (f) to (h), the symbols X and Y, which can be the same or different, are hydrogen atoms or alkyl or alkoxy radicals;

and wherein $R_1$ and $R_2$, which can be the same or different, are hydrogen or halogen atoms or alkyl, alkoxy, alkoxyl, cyclohexyl, phenyl, alkylphenyl, alkoxyphenyl, halophenyl, thienyl or furyl radicals, the alkyl moieties in the said radicals containing up to 6 carbon atoms and being straight-chained or branched, and $A^{\ominus}$ is an anion of a mono- to tribasic mineral acid, wherein said compound is administered to a subject with an asthmatic or bronchial region disease in a therapeutically effective amount.

The azoniaspironortropanol esters used according to the present invention can be prepared as follows:
 (a) demethylation of tropine to give nortropine,
 (b) reaction of nortropine with a dihalide to give a corresponding azonia compound, and
 (c) esterification of the azonia compound, wherein
 (A) the demethylation of tropine of the formula:

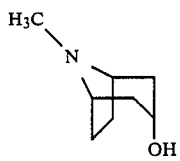
(II)

is carried out either by working in a $C_1$-$C_3$-chloroalkane which contains at least one trichloromethyl radical in the presence of an oxidation agent in basic aqueous solution or the tropine is reacted with a chloroformic acid ester in an inert solvent in the presence of an acid-binding agent to give an 8-alkoxycarbonylnortropine and this is hydrolyzed with a base in aqueous solution,
 (B) the nortropine thus obtained of the formula:

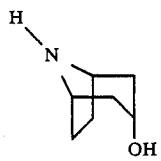
(III)

is reacted at ambient temperature for 1 or more days in a dipolar aprotic solvent with a compound of the general formula:

A—R—A in which A and R have the above-given meanings, in the presence of a secondary or tertiary amine and
 (C) the compound thus obtained for the general formula:

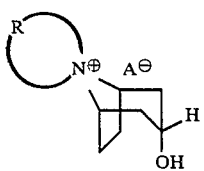
(IV)

in which R and $A^-$ have the above-given meanings, is esterified in an anhydrous, dipolar, aprotic solvent with an imidazolide of the general formula:

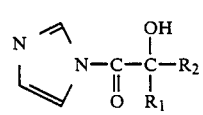
(V)

in which $R_1$ and $R_2$ have the above-given meanings, in the presence of a catalyst, and
 (D) when the radical R contains one or more olefinic double bonds in the azonium ring after passing through steps B and/or C, this unsaturated compound is optionally hydrogenated in a polar solvent with the help of a noble metal catalyst to give the corresponding saturated compound of general formula (I) in which R is a radical (a) as defined hereinbefore.

n in the above-mentioned radicals can be the same or different. In the above radicals, n is preferably so chosen that a 5- or 6-membered ring is obtained.

The anion $A^{\ominus}$ is is preferably a halide ion, such as chloride, bromide or iodide, or is a phosphate, sulphate or nitrate ion.

Examples of the radical R include the following:

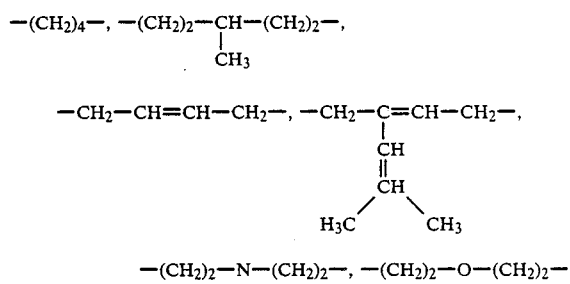

In the scope of the present invention, the alkyl radicals (including those present in alkoxy, acyl, alkylamino and the like radicals) can be straight-chained or branched and contain up to 18 carbon atoms and preferably up to 6 carbon atoms. Examples of such radicals include methyl, ethyl, n-propyl, isopropyl, n-butyl, hexyl, lauryl and stearyl radicals. The preferred acyl radicals include the acetyl and benzoyl radicals.

The preparation of the compounds used according to the present invention is described in detail in a simultaneously filed German Patent Application.

Examples of compounds which can be used according to the present invention include the following:
 1. trospium chloride [(3α-benziloyloxynortropane-8-spiro-1'-pyrrolidinium)-chloride]:
    m.p. 258°–263° C. (decomp.);
    FD-MS: m/e=392 (molecule cation);
    IR (KBr): $\gamma$=3150, 1735, 1498, 1452, 747 $cm^{-1}$.
 2. 3α-benziloyloxynortropane-8-spiro-1'-(3'-pyrrolinium)chloride;
    m.p. 267° C.; FD-MS: m/e=390 (molecule cation);
    IR (KBr): $\gamma$=1722, 1595, 1490, 1445, 741 $cm^{-1}$.
 3. 3α-benziloyloxynortropane-8-spiro-2'-isoindolinium chloride;
    m.p. 263°–265° C.; FD-MS: m/e=440 (molecule cation);
    IR (KBr): $\gamma$=1740, 747, 745, 703 $cm^{-1}$.
 4. 3α-benziloyloxynortropane-8-spiro-4'-morpholinium chloride;
    m.p. 225° C. (decomp.);
    FD-MS: m/e=408 (molecule cation);
    IR (KBr): $\gamma$=3410, 3183, 1731, 1492, 703 $cm^{-1}$.
 5. 3α-benziloyloxynortropane-8-spiro-1'-pyrrolidino[3',4'-b]quinoxalinium bromide;
    m.p. 205° C. (decomp.);
    FD-MS: m/e=492 (molecule cation);
    Ir (KBr): $\gamma$=3375, 1730, 1504, 763 $cm^{-1}$.
 6. 3α-benziloyloxynortropane-8-spiro-2'-(2'-aza-3H-phenolenium)bromide;

m.p. 322° C. (decomp.);
FD-MS: m/e=490 (molecule cation);
IR (KBr): $\gamma$=3428, 3240, 1738, 1603, 1497 cm$^{-1}$.

The compounds used according to the present invention can be applied in the form of, for example, aerosols, solutions and the like, the routes of administration being, for example, by inhalation, orally, intravenously or the like.

DETAILED DESCRIPTION OF PREFERRED EMBODIMENTS

Figure 1:
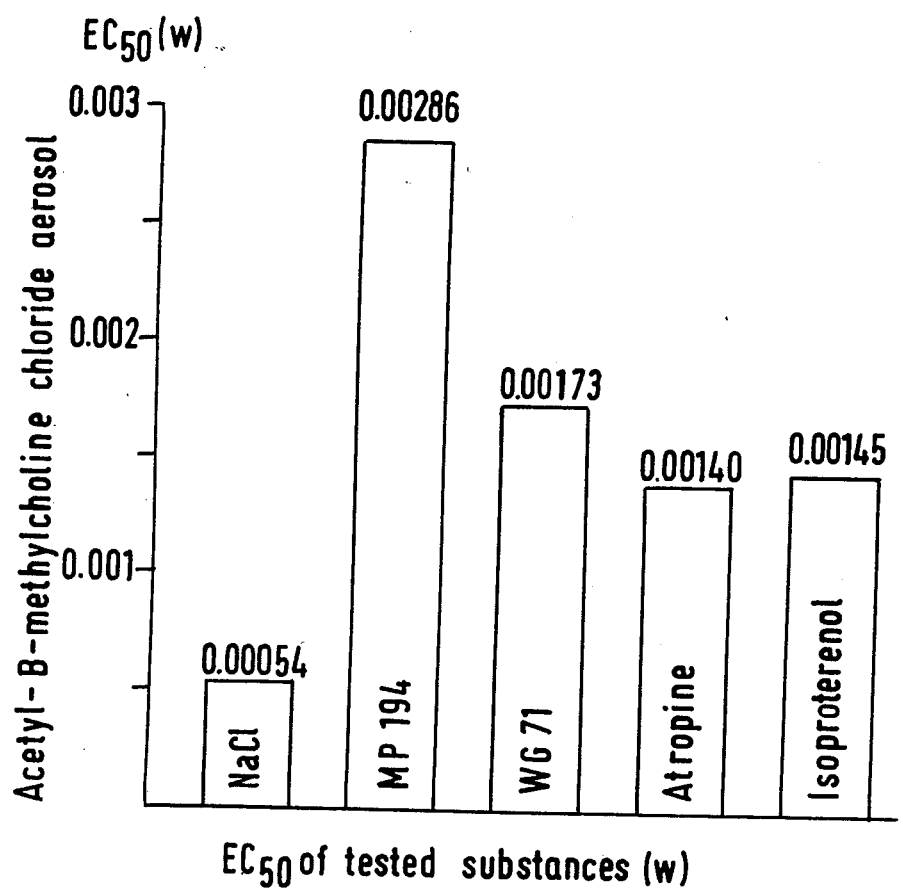
FIG. 1 shows a graph of the effective concentration ($EC_{50}$) of a provocation substance 15 minutes after intrapentoneal (i.p.) application of test substances atropine and isoproterenal.

The following Examples are given for the purpose of illustrating the present invention:

EXAMPLE 1

Inhalation Solution trospium chloride: 0.100 g.
citric acid monohydrate: 0.470 g.
trisodium citrate dihydrate: 0.530 g.
sodium chloride: 0.645 g.

The solution is prepared by successively dissolving the components in water, followed by sterilizing filtration and placing into light-protected containers. The pH value of the solution is about 4.2.

EXAMPLE 2

Dosed Aerosol trospium chloride: 0.030 g.
trichlorofluoromethane/dichlorodifluoromethane: ad 15.0 ml.

The aerosol is prepared by grinding the trospium chloride to a particle size of less than 5 $\mu$m., suspending it in cooled and liquefied propellant gas and placing into conventional aerosol containers at about 45° to 50° C. The valve on the container is so chosen that, per spray impulse, 0.1 mg. trospium chloride is applied.

EXAMPLE 3

Dosed Aerosol for Inhalation

Formulation per dosage/spray impulse:
0.1 mg. azoniaspironortropanol ester according to one of the chemical Examples
0.02 mg. Span 85 (sorbitan mono- and trifatty acid residue based on oleic acid)
10 $\mu$l. Frigen 11 (trichlorofluoromethane)
40 $\mu$l. Frigen 12 (dichlorodifluoromethane).

EXAMPLE 4

Dosed Spray for Nasal Use

Formulation per dosage/spray impulse:
2 mg. azoniaspironortropanol ester according to one of the chemical Examples
90 $\mu$l. physiological saline In order to confirm the effectiveness of the active materials according to the present invention, inhalative provocations were carried out on awake guinea pigs with a cholinergically-effective aerosol. $3 \times 10^{-7}$ mole kg$^{-1}$ of active material thereby antagonize an asthmatoid respiratory difficulty brought about by an acetyl-$\beta$-methylcholine aerosol 15 minutes after intraperitoneal administration. The therapeutic effectiveness of the active materials according to the present invention is markedly stronger than that of equimolar dosages of reference substances, such as atropine and isoproterenol.

Method

Animal Material animal type: guinea pigs
animal strain: Pirbright white
origin: Lippische Versuchstierzucht Hagemann GmbH & Co., 4923 Extertal 1, Germany
sex: male
body weight: about 500–700 g.
acclimatisation time: >8 days

Animal Maintenance living space: massive construction, conventional maintenance
room temperature: 22°±2° C.
atmospheric humidity: 50–60% relative humidity
room illumination: artificial 12 hour rhythm
cages: Macrolon lower part and wire mesh covering with feed and water containers; bedding "ssniff" from "ssniff Versuchstierdiäten GmbH, 4770 Soest, Germany
feed: Altromin-MS from Altrogge Spezialfutterwerk, Lage/Lippe, Germany; "ssniff"-MS diet and hay
drinking water: tap water ad libitum
Trospium chloride=MP 194=3$\alpha$-benziloyloxynortropane-8-spiro-1'-pyrrolidinium chloride
dehydrotrospium chloride+WG 71=3$\alpha$-benziloyloxynortropane-8-spiro-1'-(3'-pyrrolinium)-chloride

Substances, Dosages and Mode of Administration test substance: trospium chloride (MP 194) (M.W. 428)
dosage: $3 \times 10^{-7}$ mole ml$^{-1}$ kg$^{-1}$
mode of administration: intraperitoneally
test substance: dehydrotrospium chloride (WG 71) (M.W. 426)
dosage: $3 \times 10^{-7}$ mole ml$^{-1}$ kg$^{-1}$
mode of administration: intraperitoneally
reference substance: atropine hydrochloride (Serva; M.W. 325.8)
dosage: $3 \times 10^{-7}$ mole ml$^{-1}$ kg$^{-1}$
mode of administration: intraperitoneally
reference substance: isoproterenol (Fluka; M.W. 247.72)
dosage: $3 \times 10^{-1}$ mole ml$^{-1}$ kg$^{-1}$
mode of administration: intraperitoneally
control substance: physiological saline
dosage: 1 ml. kg$^{-1}$
mode of administration: intraperitoneally
further substances: acetyl-$\beta$-methylcholine chloride (Sigma; M.W. 195.7)
concentrations:
0.0316 g.$\times$100 ml$^{-1}$ double distilled water
0.0562 g.$\times$100 ml$^{-1}$ double distilled water
0.1 g.$\times$100 ml$^{-1}$ double distilled water
0.178 g.$\times$100 ml$^{-1}$ double distilled water
0.316 g.$\times$100 ml$^{-1}$ double distilled water
0.562 g.$\times$100 ml$^{-1}$ double distilled water
mode of administration: 0.5 ml. min$^{-1}$ by inhalation.

Grouping distribution to the groups: random
animals per group: 10
group division: as far as possible, on one day, animals of the experimental and control groups are taken into the experiment.

Carrying Out of the Experiments

The guinea pigs intended for an experiment are, after an acclimatization time of at least 8 days, subjected twice to an aerosol of 0.1% acetyl-$\beta$-methylcholine chloride solution since, as is known from experience, during the first two inhalative provocations, the animals react with more distinct respiratory disturbances than in the case of the subsequent provocations (adaptation). If, in the case of the two inhalation phases, a nonsensitivity (absence of respiratory disturbances) is observed towards the exposure, these animals are excluded from the actual experiment.

For the purpose of aerosol provocation, the guinea pigs are placed individually in an inhalation chamber (see Section 3.6 hereinafter) in which 0.5 ml. of solution per minute are atomized as droplet aerosol by means of a special nozzle (Rhema, Hofheim, Germany). Dependent upon the active material concentration, as well as of a pre-treatment possibly carried out, the aerosol exposure leads to a more or less marked dyspnoea, to attacks of coughing and finally to asphyxia and loss of consciousness following a tonic-clonic cramp of differing strength. With the help of a stopwatch, there is recorded the time from the commencement of inhalation to the appearance of the asphyctic state; the animals are immediately removed from the inhalation chamber and, as a rule, recover in a very short period of time (recovery of consciousness and normalization of breathing). If, within 180 seconds, no dysponea occurs, the inhalation is discontinued.

In order to demonstrate the protective action of the test and reference substances, the animals in the experiment, 15 minutes before the commencement of the inhalation, are pre-treated with these substances according to their body weight (control animals correspondingly with isotonic sodium chloride solution) and subjected to logarithmically graduated concentrations of acetyl-$\beta$-methylcholine aerosol. One aerosol concentration is tested per test day; the time between the individual aerosol provocations is at least 1 week.

Analyses And Apparatus

The inhalation chamber is a Plexiglass container specially made for this purpose, the lid of which can be closed in an air-tight manner by means of rubber sealing and grip closure means. The internal measurements of the chamber are 285×190×180 mm., which corresponds to a volume of about 9.75 liters. The special nozzle (Rhema, Hofheim, Germany, order No. 504104) is fixed to a recess on the lid and ensures a uniform supply of the available chamber space with the aerosol. The provocation solution is supplied to the nozzle via an infusion pump (Braun, Melsungen, Germany) (0.5 ml./minute) and there atomized with a superpressure of 180 kPa from an attached pressure gas bottle (artificial air, KW-free). For reasons of safety, the aerosol provocation is carried out under a ventilator.

Evaluation

For each of the tested substances (test, reference and control substances) there is taken, in the case of each investigated active material concentration, the percentage proportion of the animals reacting with dyspnoea for the calculation of the $EC_{50}$.

The $EC_{50}$, as well as the related confidence interval (p>95%), are determined from the probit regression lines of the percentage values (v. supra) provided with weight coefficients after line adaptation by the "maximum likelihood" method (10 iterations). Furthermore, there is examined the adaptation of the lines to the observed data by means of the chiquadrat test. For the evaluation, a calculation programme is commercially available (Olivetti).

Results

The tested substances, trospium chloride as well as dehydrotrospium chloride, show, after intraperitoneal administration, an outstanding broncholytic effect in the case of cholinergically-induced bronchial cramps on the awake guinea pig. The average effective concentration ($EC_{50}$) of acetyl-$\beta$-methylcholine chloride in the solution to be atomised is, in the case of the control animals, w=0.00054 (see the following Table 1). After pre-treatment with trospium chloride or dehydrotrospium chloride, the corresponding $EC_{50}$ values are w=0.00286 and w=0.00173, respectively (see the following Tables 2 and 3).

Atropine and isoproterenol were used as reference substances. For stropine and isoproterenol, there were determined average effective concentrations of the provocation substances of w=0.00138 and w=0.00145, respectively (see the following Tables 4 and 5).

Furthermore, the average effective concentrations $EC_{50}$ of the provocation substances 15 minutes after intraperitoneal administration of MP 194, WG 71, atropine and isoproterenol are illustrated schematically in FIG. 1 of the accompanying drawings.

TABLE 1

| Control substance: | NaCl (W = 0.009) |
| --- | --- |
| mode of administration: | intraperitoneal |
| dosage: | 1 ml kg$^{-1}$ |
| active material: | acetyl-$\beta$-methylcholine chloride |
| mode of administration: | by aerosol inhalation |
| concentration: | see below |

| active material concentration w | number of animals tested | number of animals reacting | probit analysis observed | reaction % calculated |
| --- | --- | --- | --- | --- |
| 0.000316 | 10 | 2 | 20.00 | 22.79 |
| 0.000562 | 10 | 5 | 50.00 | 52.35 |
| 0.000750 | 10 | 7 | 70.00 | 67.81 |
| 0.001000 | 10 | 9 | 90.00 | 80.64 |
| 0.001780 | 10 | 9 | 90.00 | 95.26 |

Test for linearity: $x^2 = 1.2629$ (FG=3)
linearity can be assumed ($\alpha \geq 0.05$)

Result of the Probit Analysis

Average effective concentration of the active material:

$EC_{50}: w = 0.000539$ confidence interval (P=0.95): 0.000339–0.000855

TABLE 2

| test substance: | trospium chloride |
| --- | --- |
| mode of administration: | intraperitoneal |
| dosage: | $3 \times 10^{-7}$ mol ml$^{-1}$ kg$^{-1}$ |
| active material: | acetyl-$\beta$-methylcholine chloride |
| mode of administration: | by aerosol inhalation |
| concentration: | see below |

| active material concentration w | number of animals tested | number of animals reacting | probit analysis observed | reaction % calculated |
| --- | --- | --- | --- | --- |
| 0.000562 | 10 | 0 | 2.50* | 5.46 |
| 0.001000 | 10 | 1 | 10.00 | 15.03 |
| 0.001780 | 10 | 5 | 50.00 | 32.00 |
| 0.003160 | 10 | 5 | 50.00 | 53.87 |
| 0.005620 | 10 | 7 | 70.00 | 74.66 |

*correction according to Bliss test for linearity: $x^2 = 2.0313$ (FG=3)
linearity can be assumed ($\alpha \geq 0.05$)

Result of the Probit Analysis average effective concentration of the active material:

$EC_{50}:w = 0.00286$ confidence interval (P=0.95): 0.00147–0.00557

TABLE 3

| test substance: | dehydrotrospium chloride |
| --- | --- |
| mode of administration: | intraperitoneal |
| dosage: | $3 \times 10^{-7}$ mol ml$^{-1}$ kg$^{-1}$ |
| active material: | acetyl-$\beta$-methylcholine chloride |
| mode of administration: | by aerosol inhalation |
| concentration: | see below |

| active material concentration w | number of animals tested | number of animals reacting | probit analysis observed | reaction % calculated |
| --- | --- | --- | --- | --- |
| 0.001000 | 10 | 3 | 30.00 | 38.74 |
| 0.001780 | 9 | 6 | 66.67 | 50.60 |
| 0.003160 | 10 | 6 | 60.00 | 62.35 |
| 0.005620 | 10 | 7 | 70.00 | 73.08 | test for linearity: $x^2 = 1.3234$ (FG=2)
linearity can be assumed ($\alpha \geq 0.05$)

Result of the Probit Analysis average effective concentration of the active material:

$EC_{50}:w = 0.00173$ confidence interval (P=0.95): 0.00031–0.00972

TABLE 4

| reference substance: | atropine chloride |
| --- | --- |
| mode of administration: | intraperitoneal |
| dosage: | $3 \times 10^{-7}$ mol ml$^{-1}$ kg$^{-1}$ |
| active material: | acetyl-$\beta$-methylcholine chloride |
| mode of administration: | by aerosol inhalation |
| concentration: | see below |

| active material concentration w | number of animals tested | number of animals reacting | probit analysis observed | reaction % calculated |
| --- | --- | --- | --- | --- |
| 0.000562 | 10 | 3 | 30.00 | 38.93 |
| 0.001000 | 10 | 6 | 60.00 | 45.98 |
| 0.001780 | 9 | 5 | 55.56 | 53.16 |
| 0.003160 | 10 | 5 | 50.00 | 60.20 |
| 0.005620 | 10 | 7 | 70.00 | 66.95 | test for linearity: $x^2 = 1.6245$ (FG=3)
linearity can be assumed ($\alpha \geq 0.05$)

Result of the Probit Analysis average effective concentration of the active material:

$EC_{50}:w = 0.00138$ confidence interval (P=0.95): 0.00022–0.00888

TABLE 5

| reference substance: | isoproterenol |
| --- | --- |
| mode of administration: | intraperitoneal |
| dosage: | $3 \times 10^{-7}$ mol ml$^{-1}$ kg$^{-1}$ |
| active material: | acetyl-$\beta$-methylcholine chloride |
| mode of administration: | by aerosol inhalation |
| concentration: | see below |

| active material concentration w | number of animals tested | number of animals reacting | probit analysis observed | reaction % calculated |
| --- | --- | --- | --- | --- |
| 0.001000 | 9 | 3 | 33.33 | 36.21 |
| 0.001780 | 8 | 5 | 62.50 | 57.88 |
| 0.003160 | 9 | 7 | 77.78 | 77.28 |
| 0.005620 | 9 | 8 | 88.89 | 90.30 | test for linearity: $x^2 = 0.1240$ (FG=1)
linearity can be assumed ($\alpha \geq 0.05$)

Result of the Probit Analysis average effective concentration of the active material:

$EC_{50}:w = 0.00145$ confidence interval (P=0.95): 0.00050–0.00426

Assessment

The test substances trospium chloride and dehydrotrospium chloride are, 15 minutes after intraperitoneal administration, comparable with or superior to the well known parasympatholytics atropine and the $\beta$-sympathomimetic isoproterenol with regard to their broncholytic effectiveness (see FIG. 1 of the accompanying drawings). From the calculations of the concentrations of acetyl-$\beta$-methylcholine chloride which, in each case, are on average effective, which is necessary for the initiation of a dyspnoea, there can be ascertained a greater effectiveness of the test substances, especially of trospium chloride, in comparison with the reference substances.

In order to test the receptor specificity of the compounds according to the present invention, the specificity of the cholinergic antagonisation must be demonstrated. A model for this is the measurement of the anticholinergic effectiveness on isolated tracheal spirals of the guinea pig.

The test substance used was 3$\alpha$-benziloyloxynortropane-8-spiro-1'-pyrrolidinium chloride (trospium chloride; MP 194), ipratropium bromide being used as comparison substance.

1. Summary.

MP 194 is competitively antagonistically effective on the isolated tracheal spirals of the guinea pig in comparison with acetyl-$\beta$-methylcholine chloride. Its strength of activity is thereby equivalent to the reference substance ipratropium bromide.

2. Interrogatory

There is to be determined the anticholinergic effectiveness of MP 194 in comparison with the reference substance ipratropium bromide on the isolated tracheal spirals of the guinea pig.

3. Method.
3.1. Animal material
3.1.1. animal species: guinea pig
3.1.2. animal strain: Pirbright white
3.1.3. origin: Hagemann GmbH & Co., 4923 Extertal 1, Germany
3.1.4. sex: male
3.1.5. body weight: about 500 g.
3.1.6. acclimatization time: >8 days
3.2. Animal maintenance
3.2.1. living space: massive construction, conventional maintenance
3.2.2. room temperature: 22°±2° C.
3.2.3. relative atmospheric humidity: 50±15%
3.2.4. room illumination: artificial dark/light rhythm in 12 hour intervals
3.2.5. animal cages: Makrolon lower part and wire mesh covering with feed and water containers; bedding "ssniff" (Versuchstierdiäten GmbH, 4770 Soest, Germany)
3.2.6. feed: "ssniff" guinea pig diet
3.2.7. drinking water: tap water ad libitum
3.3. Substances, dosaging and mode of administration
3.3.1. test substance (test antagonist)
trospium chloride (MP 194) (M.W. 428)
solvent: tyrode solution
bath concentrations:
  $1 \times 10^{-9}$ m/ml. bath solution
  $3.16 \times 10^{-9}$ M/ml. bath solution
  $1 \times 10^{-8}$ M/ml. bath solution
  $1 \times 10^{-7}$ M/ml. bath solution
administration volume: 50 μl./28 ml. bath solution
3.3.2. reference substance (reference antagonist)
ipratropium bromide (Atrovent) (M.W. 412.4)
solvent: tyrode solution
bath concentrations:
  $1 \times 10^{-9}$ M/ml. bath solution
  $3.16 \times 10^{-9}$ M/ml. bath solution
  $1 \times 10^{-8}$ M/ml. bath solution
  $1 \times 10^{-7}$ M/ml. bath solution
administration volume: 50 μl./28 ml. bath solution.
3.3.3. further substances (reference antagonists)
3.3.3.1. acetyl-β-methylcholine chloride (Sigma) (M.W. 195.7)
solvent: tyrode solution
bath concentrations:
  $1 \times 10^{-7}$ M/ml. bath solution
  $1 \times 10^{-6}$ M/ml. bath solution
  $1 \times 10^{-5}$ M/ml. bath solution
  $1 \times 10^{-4}$ M/ml. bath solution
  $1 \times 10^{-3}$ M/ml. bath solution
  $1 \times 10^{-2}$ M/ml. bath solution
  $3.16 \times 10^{-2}$ M/ml. bath solution
administration volume: 50 μl./28 ml. bath solution, cumulative
3.3.3.2. tyrode solution as nutrient medium

| component | mMole/l. | stock solution | ml. stock solution/ liter tyrode solution |
| --- | --- | --- | --- |
| NaCl | 139.2 | 58.00 g/l (1 M) | 139.2 ml. |
| KCl | 2.7 | 74.56 g/l (1 M) | 2.7 ml. |
| CaCl$_2$.2H$_2$O | 1.8 | 147.00 g/l (1 M) | 1.8 ml. |
| MgCl$_2$.6H$_2$O | 0.245 | 99.62 g/l (0.49 M) | 0.49 ml. |
| NaHCO$_3$ | 11.9 | 21.00 g/l (0.25 M) | 47.6 ml. |
| NaH$_2$PO$_4$.H$_2$O | 0.4 | 4.00 g/l (0.03 M) | 15.6 ml. |
| C$_6$H$_{12}$O$_6$ | 5.5 | — | 1.0 g. | double distilled water ad 1000 ml.

Calcium chloride is hygroscopic. Therefore, the stock solution must be titrated with the help of a Chlor-o-Counter (Marius-Chlor-o-Counter, Kipp and Zonen, 6242 Schönberg/Taunus, Germany).

In the mixing of the various stock solutions, it is to be noted that calcium precipitates out with bicarbonate and phosphate when the solutions are mixed together in high concentration. This is avoided by first diluting the 1.8 ml. of calcium chloride parent solution with about 100 ml. of double distilled water, the other stock solutions in a measurement flask already having been substantially made up with double distilled water and only then adding the calcium solution.

3.4. Grouping.
3.4.1. division into groups: random
3.4.2. number of preparations:
of the test substance group:
  n=4 ($1 \times 10^{-9}$M)
  n=2 ($3.16 \times 10^{-9}$M)
  n=2 ($1 \times 10^{-8}$M)
  n=4 ($1 \times 10^{-7}$M)
of the reference substance group:
  n=4 ($1 \times 10^{-9}$M)
  n=2 ($3.16 \times 10^{-9}$M)
  n=2 ($1 \times 10^{-8}$M)
  n=4 ($1 \times 10^{-7}$M).

3.5. Carrying out of the experiments

The guinea pig is stunned by a blow on the neck. Subsequently, the whole of the trachea is roughly freed beginning from the larynx up to the tracheal bifurcation, removed and transferred to tempered (37° C.) and carbogenized tyrode solution. After surrounding connective tissue has been removed as far as possible, the preparation is cut up spirally by means of fine scissors at an angle of about 45° and separated into two equal sized sections. After weighing, both preparations are provided proximally and distally with a silk thread. One thread serves for fixing the preparation by means of a loop to the bottom of the bath and the other is connected via a hook with the transducer above the bath vessel.

Subsequently, the preparations, corresponding to the calibration, are prestressed with about 80 mN and equilibrated from 50-100 minutes. During the equilibration phase, the nutrient solution in the bath vessels is renewed in 15 minute intervals. As soon as the resting muscle tonus of the preparation has stabilized, there takes place the cumulative addition of the agonist, whereby the addition of the next highest concentration first takes place when no further increase of contraction is recognisable (plateau). When the maximum contraction height of the preparation is achieved, the cumulative agonist addition is ended and the preparation is rinsed. After a further equilibration phase (v. supra), the cumulative addition of the agonist is repeated but this time in the presence of the test or reference antagonist.

3.6. Analyses and apparatus.

3.6.1. The perfusion part consists of an L-shaped organ bath in the hollow space of which (longer limb) runs a double glass spiral through which the nutrient solution is passed into the actual bath vessel (28 ml. content; shorter limb). This bath vessel is divided into two chambers which are, however, connected together by two transverse connections. Thus, the supply of the organ with Carbogen (95% oxygen and 5% carbon dioxide) can take place indirectly from the smaller rearmost of the two chambers, whereby the organ does not hang directly in the Carbogen inflow which, inter alia, makes possible a more precise recordal of the organ reactions. The inlet chambers as well as the feeding glass spirals are tempered from the outside to 37° C. by a separate liquid circulation. This tempering takes place with the help of a "Colora" ultra-thermostat type K (Colora Messtechnik GmbH, Dusseldorf, Germany) which serves as thermostat and pump. In order, in case of need, always to have available ready-for-use nutrient solution, above the organ bath is provided a double-walled storage container in which the nutrient solution is also tempered and carbogenised. This is connected via a glass stopcock and a polypropylene tube with double glass spiral in the interior of the organ bath.

3.6.2. The measurement and recording part includes a transducer (Statham-Universal-Zelle UC-2; Hugo Sachs Elektronic KG, Hugstetten, Germany). By means of a hanging-in weight, a force of 40 mN is produced on the transducer which passes as electrical signal via a connecting cable to a bridge amplifier. The amplification is smoothly so regulated that the force provided corresponds to a constant value on the scale or an analogous value on the millimeter paper of the recorder (dependent upon the amplification; see below). After fixing the organ, the preparation is prestressed to the doubled mark, corresponding to 80 mN. The recorder connected with the amplifier (Hellige, Freiburg/Breisgau, Germany) records all analogue signals on thermosensitive paper with millimeter divisions. The recorder amplification is thereby so regulated that the pulling force of the weight (40 mN) on the transducer corresponds to an indicator stroke of 4 cm. (calibration: force produced by means of the weight $\hat{=}$ 4 cm. on the analogue protocol).

3.7. Evaluation.

The cumulative addition of the agonist leads on the isolated tracheal spiral to a dosage-dependent contraction force increase which is recorded proportionally on the analogue recorder (see calibration). From these analogue protocols is carried out the quantitative evaluation of the cumulative dosage action curves according to the method of van Rossum (1963). For this purpose, the absolute measurement data (in [mm]) is first converted on the basis of the maximum effect ($E_{Am}$ or $E_{AmB}$), which is taken as being 100%, into percentage values. By means of non-linear regression, from these data there is determined for each individual preparation the ratio of the molar concentrations of the agonists (quotient=x) which are necessary in order precisely to achieve half of the maximum effect in the presence and absence of the test or reference antagonists of the molar concentration [B] ($-\log [B] = pa_x$). On the basis of the formula $pA_2 = pA_x \log (x-1)$ (Ariens and Schild, 1957), there is determined the negative decadic logarithm of the molar antagonist concentration ($pA_2$) in the case of which x corresponds to the value of 2, i.e. in the case of the presence of antagonists in the appropriate molar concentration, the molar agonist concentration must be doubled in order to achieve the same effect as without the action of the antagonists. The quality of the antagonism (competitive/non-competitive) is tested statistically on the basis of the comparison of the maximum effect in the absence ($E_{Am}$) and presence ($E_{AmB}$) of the test or reference antagonists. (t-test with paired arrangement). Finally, the difference of the $pA_2 \pm s$ between test and reference antagonist is examined for significance (t-test of two independent samples).

4. Results.

Figure 2:
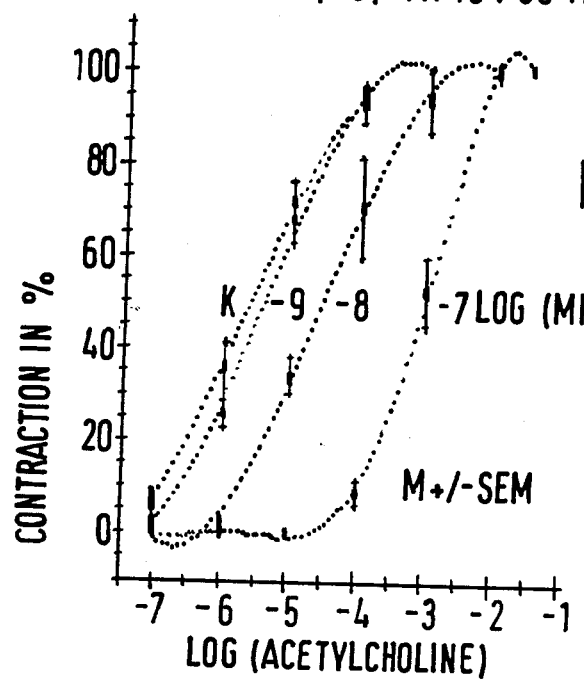
FIG. 2 demonstrates the dosage dependent antagonism of tests substances atropine and epratropium bromide against acetyl-$\beta$-methylcholine chloride.
Figure 3:
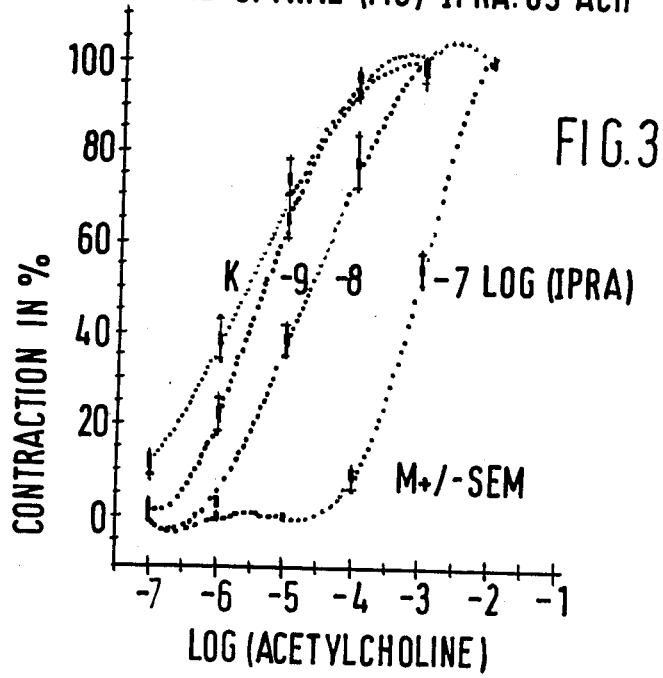

MP 194 and ipratropium bromide (Atrovent) show on isolated tracheal spirals from the guinea pig a comparable, dosage-dependent antagonism against the cholinergic agonist acetyl-$\beta$-methylcholine chloride (see FIG. 2 of the accompanying drawings). The $pA_2 \pm s$ determined for MP 194 of 9.26±0.29 does not differ significantly from the $pA_2 \pm s$ for ipratropium bromide of 9.31±0.39 (see Table 1).

The quality of the antagonism is competitive not only in the case of MP 194 but also in the case of ipratropium bromide, on the basis of the comparison between the maximum effects in the case of the absence and presence of the antagonist in equation (see the following Table 6).

5. Assessment.

The investigation demonstrates the clear anticholinergic effectiveness of MP 194 on isolated tracheal spirals from the guinea pig and thus supplements the earlier investigations of effectiveness on the awake animal. The better quantification of the results of the in vitro models also permits the conclusion that MP 194 is, with regard to the strength of action, equal to the reference substance ipratropium bromide (see the $pA_2$ values). Furthermore, on the basis of the investigation, a competitive antagonism of both substances can be assumed (see $E_{AmB}/E_{Am}$).

TABLE 6

|  | MP 194 | ipratropium bromide |
| --- | --- | --- |
| $pA_2 \pm s$ | 9.26 ± 0.29 | 9.31 ± 0.39 |
| $E_{AmB}/E_{Am} \pm s$ | 1.09 ± 0.22 | 1.10 ± 0.24 |

We claim:

1. Method of treating asthmatic diseases and diseases of the bronchial region comprising administering to a subject with said disease a therapeutically effective amount of a compound selected from the group consisting of:
   3α-benziloyloxynortropane-8-spiro-1'-pyrrolidinium chloride,
   3α-benziloyloxynortropane-8-spiro-1'-(3'-pyrrolinium)chloride,
   3α-benziloyloxynortropane-8-spiro-2'-isoindolinium chloride,
   3α-benziloyloxynortropane-8-spiro-4'-morpholinium chloride,
   3α-benziloyloxynortropane-8-spiro-1'-pyrrolidino-[3',4'-b]quinoxalinium bromide, and
   3α-benziloyloxynortropane-8-spiro-2'-(2'-aza-3H-phenolenium)bromide.

2. Method of claim 1, wherein said compound is 3α-benziloyloxynortropane-8-spiro-1'-pyrrolidinium chloride.

3. Method of claim 1, wherein said compound is administered.

4. Method of claim 1, wherein said compound is administered via aerosol.

5. Method of claim 1, wherein said compound is administered in an amount of about 0.1 mg per dose.

6. Method of claim 1, wherein said compound is administered in an amount of about 2.0 mg per dose.

7. Method of claim 1, wherein said compound is administered intravenously.

8. Method of claim 1, wherein said compound is administered orally.

9. Method of treating asthmatic diseases of the bronchial region comprising administering to a subject with said disease 3α-benziloyloxynortropone-8-spiro-1'-pyrrolidinium chloride and a pharmaceutically acceptable carrier in an amount from about 0.1 mg to about 2.0 mg of said compound per dose, wherein said compound is administered in the form of a nasal spray.

* * * * *

UNITED STATES PATENT AND TRADEMARK OFFICE
CERTIFICATE OF CORRECTION

PATENT NO. : 4,780,476
DATED : October 25, 1988
INVENTOR(S) : Wolf Grimminger, et al.

It is certified that error appears in the above-identified patent and that said Letters Patent is hereby corrected as shown below:

Column 2, line 68: change "alkoxyl" to -- alkoyl --.

Column 4, line 56: change "747" to -- 757 --.

Column 11, line 38: change "m/ml" to -- M/ml --.

Column 14, line 27: change "equation" to -- question --.

Column 14, line 68: after "administered" add -- via inhalation --.

Signed and Sealed this

Twenty-fifth Day of July, 1989

*Attest:*

DONALD J. QUIGG

*Attesting Officer*      *Commissioner of Patents and Trademarks*